(12) United States Patent 
Lee et al.

(10) Patent No.: US 8,354,424 B2
(45) Date of Patent: Jan. 15, 2013

(54) METHOD OF TREATING ACTINIC KERATOSIS

(75) Inventors: James H. Lee, St. Paul, MN (US); Terrance L. Fox, Oakdale, MN (US)

(73) Assignee: Medicis Pharmaceutical Corporation, Scottsdale, AZ (US)

( * ) Notice: Subject to any disclaimer, the term of this patent is extended or adjusted under 35 U.S.C. 154(b) by 1013 days.

(21) Appl. No.: 11/886,204

(22) PCT Filed: Mar. 14, 2006

(86) PCT No.: PCT/US2006/008868
§ 371 (c)(1),
(2), (4) Date: Jun. 4, 2008

(87) PCT Pub. No.: WO2006/099275
PCT Pub. Date: Sep. 21, 2006

(65) Prior Publication Data
US 2008/0262022 A1  Oct. 23, 2008

Related U.S. Application Data

(60) Provisional application No. 60/661,661, filed on Mar. 14, 2005.

(51) Int. Cl.
*A61K 31/44* (2006.01)
*A61K 31/4965* (2006.01)

(52) U.S. Cl. ........................ 514/293; 514/255
(58) Field of Classification Search .............. 514/255
See application file for complete search history.

(56) References Cited

U.S. PATENT DOCUMENTS

| 3,314,941 A | 4/1967 | Littell et al. |
| 3,764,681 A | 10/1973 | Dreikorn |
| 3,917,624 A | 11/1975 | Abu El-Haj et al. |
| 4,689,338 A | 8/1987 | Gerster |
| 4,698,348 A | 10/1987 | Gerster |
| 4,929,624 A | 5/1990 | Gerster et al. |
| 4,988,815 A | 1/1991 | Andre et al. |
| 5,037,986 A | 8/1991 | Gerster |
| 5,175,296 A | 12/1992 | Gerster |
| 5,238,944 A | 8/1993 | Wick et al. |
| 5,266,575 A | 11/1993 | Gerster et al. |
| 5,268,376 A | 12/1993 | Gester |
| 5,346,905 A | 9/1994 | Gerster |
| 5,352,784 A | 10/1994 | Nikolaides et al. |
| 5,367,076 A | 11/1994 | Gerster |
| 5,389,640 A | 2/1995 | Gerster et al. |
| 5,395,937 A | 3/1995 | Nikolaides et al. |
| 5,446,153 A | 8/1995 | Lindstrom et al. |
| 5,482,936 A | 1/1996 | Lindstrom |
| 5,693,811 A | 12/1997 | Lindstrom |
| 5,741,908 A | 4/1998 | Gerster et al. |
| 5,756,747 A | 5/1998 | Gerster |
| 5,922,884 A | 7/1999 | Huang et al. |
| 5,939,090 A | 8/1999 | Beaurline et al. |
| 6,039,969 A | 3/2000 | Tomai et al. |
| 6,069,149 A | 5/2000 | Nanba et al. |
| 6,083,505 A | 7/2000 | Miller et al. |
| 6,107,322 A | 8/2000 | Huang et al. |
| 6,110,929 A | 8/2000 | Gerster et al. |
| 6,194,425 B1 | 2/2001 | Gerster et al. |
| 6,245,776 B1 | 6/2001 | Skwierczynski et al. |
| 6,331,539 B1 | 12/2001 | Crooks et al. |
| 6,376,669 B1 | 4/2002 | Rice et al. |
| 6,433,002 B2 | 8/2002 | Huang et al. |
| 6,451,810 B1 | 9/2002 | Coleman et al. |
| 6,514,985 B1 | 2/2003 | Gerster et al. |
| 6,518,265 B1 | 2/2003 | Kato et al. |
| 6,518,280 B2 | 2/2003 | Gerster et al. |
| 6,525,064 B1 | 2/2003 | Dellaria et al. |
| 6,541,485 B1 | 4/2003 | Crooks et al. |
| 6,545,016 B1 | 4/2003 | Dellaria et al. |
| 6,545,017 B1 | 4/2003 | Dellaria et al. |
| 6,558,951 B1 | 5/2003 | Tomai et al. |
| 6,573,273 B1 | 6/2003 | Crooks et al. |
| 6,608,093 B2 | 8/2003 | Huang et al. |
| 6,624,172 B2 | 9/2003 | Lindstrom et al. |
| 6,656,938 B2 | 12/2003 | Crooks et al. |
| 6,660,735 B2 | 12/2003 | Crooks et al. |
| 6,660,747 B2 | 12/2003 | Crooks et al. |
| 6,664,264 B2 | 12/2003 | Dellaria et al. |
| 6,664,265 B2 | 12/2003 | Crooks et al. |
| 6,667,312 B2 | 12/2003 | Bonk et al. |
| 6,670,372 B2 | 12/2003 | Charles et al. |
| 6,677,347 B2 | 1/2004 | Crooks et al. |
| 6,677,348 B2 | 1/2004 | Heppner et al. |
| 6,677,349 B1 | 1/2004 | Griesgraber |
| 6,683,088 B2 | 1/2004 | Crooks et al. |
| 6,693,113 B2 | 2/2004 | Lindstrom |
| 6,706,728 B2 | 3/2004 | Hedenstrom et al. |
| 6,743,920 B2 | 6/2004 | Lindstrom et al. |
| 6,747,040 B2 | 6/2004 | Lindstrom et al. |

(Continued)

FOREIGN PATENT DOCUMENTS

| EP | 0 394 026 | 10/1990 |
| EP | 1 104 764 | 6/2001 |
| EP | 1512685 A1 * | 3/2005 |

(Continued)

OTHER PUBLICATIONS

Nonproprietary name adopted by the USAN Council, Sotirimod.*

(Continued)

*Primary Examiner* — Sreeni Padmanabhan
*Assistant Examiner* — Timothy E Betton
(74) *Attorney, Agent, or Firm* — Len S. Smith; Marlan D. Walker

(57) ABSTRACT

A method of treating actinic keratosis including applying topically to an actinic keratosis lesion twice per week for a duration of 8 weeks a formulation comprising 2-methyl-1-(2-methylpropyl)-1H-imidazo[4,5-c][1,5]naphthyridin-4-amine.

31 Claims, 11 Drawing Sheets

U.S. PATENT DOCUMENTS

Figure 1:
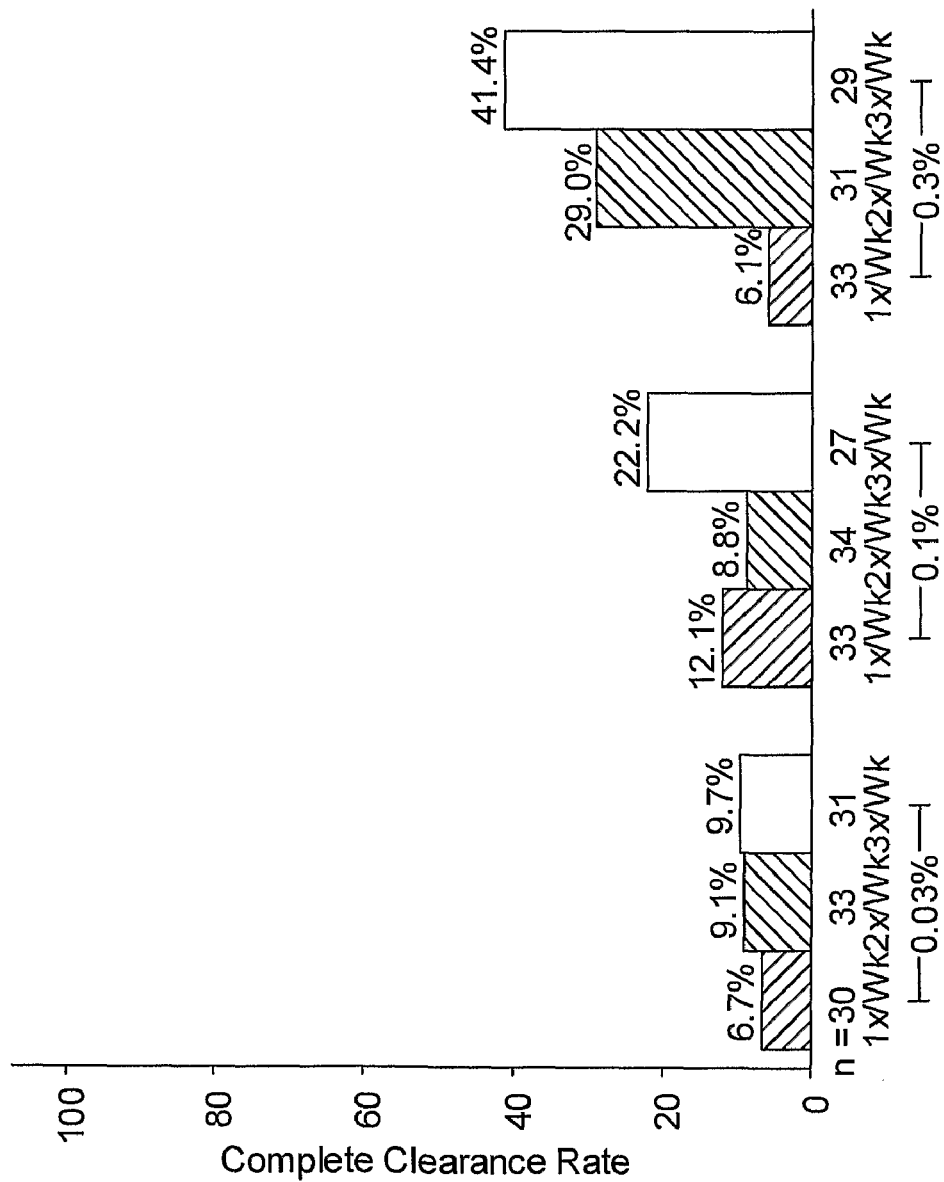

| | | | |
|---|---|---|---|
| 6,756,382 B2 | 6/2004 | Coleman et al. | |
| 6,797,718 B2 | 9/2004 | Dellaria et al. | |
| 6,818,650 B2 * | 11/2004 | Griesgraber | 514/293 |
| 6,894,165 B2 | 5/2005 | Gerster et al. | |
| 6,949,646 B2 | 9/2005 | Gerster et al. | |
| 2002/0016332 A1 | 2/2002 | Slade | |
| 2002/0055517 A1 | 5/2002 | Smith | |
| 2002/0110840 A1 | 8/2002 | Tomai et al. | |
| 2003/0130299 A1 | 7/2003 | Crooks et al. | |
| 2003/0133913 A1 | 7/2003 | Tomai et al. | |
| 2003/0139364 A1 | 7/2003 | Krieg et al. | |
| 2003/0161797 A1 | 8/2003 | Miller et al. | |
| 2003/0199538 A1 * | 10/2003 | Skwierczynski et al. | 514/291 |
| 2003/0212127 A1 * | 11/2003 | Glassman et al. | 514/458 |
| 2004/0014779 A1 | 1/2004 | Gorden et al. | |
| 2004/0043946 A1 * | 3/2004 | Popp | 514/35 |
| 2004/0091491 A1 | 5/2004 | Kedl et al. | |
| 2004/0132079 A1 | 7/2004 | Gupta et al. | |
| 2004/0141950 A1 | 7/2004 | Noelle et al. | |
| 2004/0147543 A1 | 7/2004 | Hays et al. | |
| 2004/0162309 A1 | 8/2004 | Gorden et al. | |
| 2004/0171086 A1 | 9/2004 | Fink et al. | |
| 2004/0175336 A1 | 9/2004 | Egging et al. | |
| 2004/0176367 A1 | 9/2004 | Griesgraber et al. | |
| 2004/0180919 A1 | 9/2004 | Miller et al. | |
| 2004/0181130 A1 | 9/2004 | Miller et al. | |
| 2004/0181211 A1 | 9/2004 | Graham et al. | |
| 2004/0191833 A1 | 9/2004 | Fink et al. | |
| 2004/0192585 A1 | 9/2004 | Owens et al. | |
| 2004/0197865 A1 | 10/2004 | Gupta et al. | |
| 2004/0202720 A1 | 10/2004 | Wightman et al. | |
| 2004/0214851 A1 | 10/2004 | Birmachu et al. | |
| 2004/0235881 A1 | 11/2004 | Mitra et al. | |
| 2005/0054590 A1 | 3/2005 | Averett | |
| 2010/0092401 A1 | 4/2010 | Vallejo et al. | |

FOREIGN PATENT DOCUMENTS

| | | |
|---|---|---|
| EP | 1889609 A2 * | 2/2008 |
| JP | 9-208584 | 8/1997 |
| JP | 9-255926 | 3/1999 |
| JP | 11-222432 | 8/1999 |
| JP | 2000-247884 | 9/2000 |
| WO | WO 01/74343 | 10/2001 |
| WO | WO 02/36592 | 5/2002 |
| WO | WO 02/46194 | 6/2002 |
| WO | WO 02/46749 | 6/2002 |
| WO | WO 02/102377 | 12/2002 |
| WO | WO 03/020889 | 3/2003 |
| WO | WO 03/043572 | 5/2003 |
| WO | WO 03/045391 | 6/2003 |
| WO | WO 03/097641 | 11/2003 |
| WO | WO 2004/091500 | 10/2004 |
| WO | WO-2008/010963 A2 | 1/2008 |

OTHER PUBLICATIONS

Wagner, et al., "Induction of Cytokines in Cynomoglus Monkeys by the Immune Response Modifiers, Imiquimod, S-27609 and S-28463", Cytokine, 9(11), pp. 837-845 (1997).

Wermuth, "Molecular Variations Based on Isosteric Replacements", The Practice of Medicinal Chemistry, pp. 203-237 (1996).

State of the Art Report, No. 351, dated Jun. 30, 2010.

Wozniak, et al, "The Amination of 3-nitro-1, 5-naphthyridines by Liquid Ammonia/Potassium Permanganate[1,2]. A New and Convenient Amination Method.", Journal of the Royal Netherlands, Chemical Society, 102, pp. 511-513, Dec. 12, 1983.

Brennan, et al., "Automated Bioassay of Interferons in Micro-test Plates", Biotechniques, Jun./Jul. 78, 1983.

Testerman, et al., "Cytokine Induction by the Immunomodulators Imiquimod and S-27609", Journal of Leukocyte Biology, vol. 58, pp. 365-372, Sep. 1995.

Bachman, et al, "Synthesis of Substituted Quinolylamines. Derivatives of 4-Amino-7-Chloroquinoline", J. Org. Chem, 15, pp. 1278-1284 (1950).

Jain, et al, Chemical and Pharmacological Investigations of Some ω-Substituted Alkylamino-3- aminopyridines°, J. Med. Chem., 11, pp. 87-92 1968.

Baranov, et al., Chem. Abs. 85, 94362, (1976).

Berényi, et al, "Ring Transformation of Condensed Dihydro-astriazines", J. Heterocyclic Chem., 18, pp. 1537-1540 (1981).

Chollet, et al, "Development of a Topically Active Imiquimod Formulation",Pharmaceutical Development and Technology, 4(1), pp. 35-43 (1999).

Izumi, et al., "1H-Imidazo[4,5-c]guinoline Derivatives as Novel Potent TNF-a Suppressors: Synthesis and Structure-Activity Relationship of 1-, 2- and 4-Substituted 1H-imidazo[4,5- c]pyridines", Bioorganic & Medicinal Chemistry, 11, pp. 2541-2550 (2003).

Hart, E.P. "Naphthyridines. Hydroxynaphthyridines", Journal of the Chemical Society, Part III, pp. 212-214 (1956).

Oct. 7, 2011 e-mail from Stephanie C. Shubat, M.S. (Director, USAN Program) with attached PDF of U.S. Adopted Names Internal Adoption Statement for Sotirimod (dated Apr. 27, 2005).

Screenshot of U.S. Adopted Names (USAN) Statement on Sotirimod Showing Document earliest date on "Tuesday, May 3, 2005, 11:51:00 am" (screenshot printed on Oct. 7, 2011).

Screenshot of U.S. Adopted Names (USAN) Statement on Sotirimod Showing Document earliest date on "Friday, Jun. 24, 2005, 2:46:00 pm" (screenshot printed on Oct. 7, 2011).

* cited by examiner

METHOD OF TREATING ACTINIC KERATOSIS

CROSS-REFERENCES TO RELATED APPLICATIONS

This application is a 35 U.S.C. §371 national stage of PCT application PCT/US2006/008868, filed Mar. 14, 2006, which claims benefit of priority to U.S. provisional application 60/661,661, filed Mar. 14, 2005, the entire contents of each of these applications being hereby incorporated by reference.

FIELD

The present invention relates to topical treatment of actinic keratosis lesions using immune response modifier compounds.

BACKGROUND

In the 1950's the 1H-imidazo[4,5-c]quinoline ring system was developed, and 1-(6-methoxy-8-quinolinyl)-2-methyl-1H-imidazo[4,5-c]quinoline was synthesized for possible use as an antimalarial agent. Subsequently, syntheses of various substituted 1H-imidazo[4,5-c]quinolines were reported. For example, 1-[2-(4-piperidyl)ethyl]-1H-imidazo[4,5-c]quinoline was synthesized as a possible anticonvulsant and cardiovascular agent. Also, several 2-oxoimidazo[4,5-c]quinolines have been reported.

Certain 1H-imidazo[4,5-c]quinolin-4-amines and 1- and 2-substituted derivatives thereof were later found to be useful as antiviral agents, bronchodilators and immunomodulators. Subsequently, certain substituted 1H-imidazo[4,5-c]pyridin-4-amine, quinolin-4-amine, tetrahydroquinolin-4-amine, naphthyridin-4-amine, and tetrahydronaphthyridin-4-amine compounds as well as certain analogous thiazolo and oxazolo compounds were synthesized and found to be useful as immune response modifiers, rendering them useful in the treatment of a variety of disorders.

Pharmaceutical formulations containing IRM compounds are disclosed in U.S. Pat. Nos. 5,238,944; 5,939,090; and 6,425,776; European Patent 0 394 026; and U.S. Patent Publication 2003/0199538. Many such formulations include preservatives such as methylparaben, sorbic acid, propylene glycol, etc.

The mechanism for the antiviral and antitumor activity of these IRM compounds is thought to be due in substantial part to enhancement of the immune response by induction of various important cytokines (e.g., interferons, interleukins, tumor necrosis factor, etc.). Such compounds have been shown to stimulate a rapid release of certain monocyte/macrophagederived cytokines and are also capable of stimulating B cells to secrete antibodies, which play an important role in these IRM compounds' antiviral and antitumor activities. One of the predominant immunostimulating responses to these compounds is the induction of interferon (IFN)-α production, which is believed to be very important in the acute antiviral and antitumor activities seen. Moreover, up regulation of other cytokines, such as, for example, tumor necrosis factor (TNF), Interleukin-1 (IL-1) and IL-6 also have potentially beneficial activities and are believed to contribute to the antiviral and antitumor properties of these compounds.

Accordingly, in view of their importance and potential benefit, there is a continuing need for new formulations and treatments using these unique compounds.

SUMMARY OF THE INVENTION

Although some of the beneficial effects of IRMs are known, the ability to provide therapeutic benefit via topical application of an IRM compound for treatment of a particular condition at a particular location may be hindered by a variety of factors. These factors include: irritation of the skin to which the formulation is applied; formulation wash away; insolubility and/or degradation of the IRM compound in the formulation; physical instability of the formulation (e.g., separation of components, thickening, precipitation/agglomerization of active ingredient, and the like); poor permeation; undesired systemic delivery of the topically applied IRM compound; concentration of the IRM compound applied; frequency of application; and duration of application.

The present invention provides methods of treating actinic keratosis (AK). Actinic keratoses are premalignant lesions considered biologically to be either carcinoma in-situ or squamous intraepidermal neoplasia. AK is the most frequent epidermal tumor and is induced by ultraviolet (UV) radiation, typically from sunlight. Because of its precancerous nature, AK may be considered the most important manifestation of sun-induced skin damage.

The method includes applying topically to a surface (e.g., dermal or mucosal surface) of a patient in need thereof (i.e., a patient with actinic keratosis lesions) a pharmaceutical formulation that includes 2-methyl-1-(2-methylpropyl)-1H-imidazo[4,5-c][1,5]naphthyridin-4-amine.

It has been discovered that surprisingly desirable results with respect to important properties (e.g., a high level of efficacy and a low level of side effects) occur with a formulation that includes about 0.3-wt-%-2-methyl-1-(2-methylpropyl)-1H-imidazo[4,5-c][1,5]naphthyridin-4-amine applied twice per week to the actinic keratosis lesions for a duration of about 8 weeks. This is compared to other formulations of the same compound applied using the same treatment regimen or compared to the same formulation of the same compound using different treatment regimens.

The amount of 2-methyl-1-(2-methylpropyl)-1H-imidazo[4,5-c][1,5]naphthyridin-4-amine present in a topical formulation of the invention will be about 0.3 wt-%, based on the total weight of the formulation. The formulations can be prepared using the free base form or salts of 1-(2-methylpropyl)-1H-imidazo[4,5-c][1,5]naphthyridin-4-amine. The salt form is used in an amount sufficient to provide the equivalent of about 0.3% by weight of the free base.

In certain embodiments, it has been found that formulations containing IRM compounds such as 2-methyl-1-(2-methylpropyl)-1H-imidazo[4,5-c][1,5]naphthyridin-4-amine in combination with sorbic acid may suffer impaired stability of both the IRM compound and the sorbic acid. However, it has further been found that addition of a pharmaceutically acceptable antioxidant compound to such formulations can reduce degradation of the IRM compound and sorbic acid, thereby providing improved stability.

Sorbic acid and related salts and esters are often used as preservative systems and can be particularly suitable for use in a multi-dose dispenser formulation (see, for example, U.S. Pat. No. 6,245,776 (Skwierczynski et al.)), but stability is an important issue for formulations and can reduce shelf life of a product or even jeopardize regulatory approvability. It has been discovered that stability can be improved through the addition of a compound acting as an antioxidant. The antioxidant may beneficially have hydrogen atom donating functionality. Moreover, when an antioxidant compound is included with the IRM compound and sorbic acid, stability of the formulation may be further improved by adding a chelating agent.

In one embodiment, the method of the present invention use a pharmaceutical formulation that includes: about 0.3 by weight (wt-%) 2-methyl1(2-methylpropyl)-1H-imidazo[4,5- c][1,5]naphthyridin-4-amine; a preservative system that includes sorbic acid, esters thereof, salts thereof, or combinations thereof; and an antioxidant. A chelating agent may also beneficially be included.

In another embodiment, the method of the present invention uses a pharmaceutical formulation that includes: about 0.3 wt % 2-methyll(2-methylpropyl)-1Himidazo[4,5-c][1,5] naphthyridin-4-amine; a preservative system that includes a sorbic acid preservative selected from the group consisting of sorbic acid, esters thereof, salts thereof, and combinations thereof; an antioxidant (preferably having hydrogen atom donating functionality); a fatty acid; and a hydrophobic, aprotic component miscible with the fatty acid and having a hydrocarbyl group of 7 or more carbon atoms. A chelating agent may also beneficially be included.

In another embodiment, the method of the present invention uses a pharmaceutical formulation that includes: about 0.3 wt-% 2-methyl-1-(2-methylpropyl)-1H-imidazo[4,5-c][1,5]naphthyridin-4-amine; 0.001% by weight to 0.2% by weight of an antioxidant having hydrogen atom donating functionality; 0 to 0.1% by weight of a chelating agent; 1% by weight to 30% by weight of a fatty acid; 1% by weight to 15% by weight of a medium-chain triglyceride; 0.2% by weight to 2.0% by weight of a viscosity enhancing agent; 0.1% by weight to 6.0% by weight of an emulsifier; and water; wherein the formulation has a pH of 4.0 to 6.0 and the weight percentages are based on the total weight of the formulation. In this embodiment, the preservative system includes: 0.02% by weight to 0.2% by weight of a sorbic acid preservative selected from the group consisting of sorbic acid, esters thereof, salts thereof, and combinations thereof; 0 to 10.0% by weight of a preservative enhancing solubilizer; and 0.05% by weight to 0.2% by weight of a secondary preservative compound.

As used herein, a "sorbic acid preservative" means sorbic acid, esters of sorbic acid, salts of sorbic acid, or combinations thereof.

As used herein "remains substantially constant" means that the concentration of sorbic acid preservative in an IRM-containing formulation does not decrease by more than 15% of the initial concentration (i.e., its concentration when initially formulated) when stored for at least 6 months at 40° C. and 75% relative humidity.

As used herein, "a" or "an" or "the" are used interchangeably with "at least one," to mean "one or more" of the listed element.

Also herein, all numerical values are set forth with the number of significant figures representing the level of accuracy desired in the measurement considering the standard deviation found in their respective testing measurements.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

The present invention provides methods that include applying topically (e.g., to a dermal or mucosal surface) of a patient in need thereof (i.e., a patient with actinic keratosis lesions) a pharmaceutical formulation that includes 2-methyl-1-(2-methylpropyl)1H-imidazo[4,5-c][1,5] naphthyridin4amine.

It has been discovered that significant results occur with a formulation that includes 0.3 wt-% (upon addition) 2-methyl-1-(2-methylpropyl)-1H-imidazo[4,5-c][1,5]naphthyridin 4-amine applied twice per week to the actinic keratosis lesions for a duration of about 8 weeks compared to other formulations of the same compound applied using the same treatment regimen or compared to the same formulation of the same compound using different treatment regimens.

Formulations according to the present invention can be applied to any suitable location, for example topically to dermal and/or mucosal surfaces, or internally to a particular tissue location having actinic keratosis lesions. In the case of dermal application, the therapeutic effect of the IRM compound typically extends only to the superficial layers of the dermal surface or to tissues below the dermal surface. Thus, another aspect of the present invention is directed to a method for the treatment of actinic keratosis lesions by applying to skin or other surface including AK lesions one of the formulations described herein. Herein "actinic keratosis lesions" also includes pre-actinic keratosis lesions.

In general, the amount of 2-methyl-I-(2-methylpropyl)-1H-imidazo[4,5-c][1,5]naphthyridin-4-amine present in a topical formulation of the invention will be about 0.3 wt-% upon addition, based on the total weight of the formulation. Herein "upon addition" means that the amount of the compound is reported as that amount added to the formulation upon preparation of the formulation. The formulations used in the examples below were prepared using the free base form of 1-(2-methylpropyl)-1H-imidazo[4,5-c][1,5]naphthyridin-4-amine. Alternatively, formulations can be prepared using a pharmaceutically acceptable salt of 1-(2-methylpropyl)-1H-imidazo[4,5-c][1,5]naphthyridin-4-amine. The salt form is used in an amount sufficient to provide the equivalent of about 0.3% by weight of 1-(2-methylpropyl)-1H-imidazo[4,5-c][1, 5]naphthyridin-4-amine free base. For example, a formulation prepared using 0.34% by weight of the hydrochloride salt of 1-(2-methylpropyl)-1H-imidazo[4,5-c][1,5]naphthyridin-4-amine would contain the equivalent of about 0.3% 1-(2-methylpropyl)-1H-imidazo[4,5-c][1,5]naphthyridin-4-amine free base.

Formulations used in delivering 2-methyll(2-methylpropyl)1Himidazo[4,5-c][1,5]naphthyridin-4-amine can include a preservative system, an antioxidant, a chelating agent, a fatty acid, a hydrophobic component, a viscosity enhancing agent, an emulsifier, a pH adjuster, and combinations thereof.

In certain embodiments, formulations used in delivering 2-methyll(2-methylpropyl)1H-imidazo[4,5-c][1,5]naphthyridin-4-amine typically include a preservative system that includes a sorbic acid preservative (i.e., sorbic acid, esters of sorbic acid, salts of sorbic acid, or combinations thereof). Surprisingly, such formulations are stabilized through the incorporation of an antioxidant, more preferably an antioxidant having hydrogen atom donating functionality. Additional stability, particularly of the antioxidant, can be obtained through the incorporation of a chelating agent.

Through the use of an antioxidant and an optional chelating agent, the concentration of the sorbic acid preservative in an IRM-containing formulation remains substantially constant relative to its initial concentration (i.e., its concentration when initially formulated) when stored for at least 6 months at 40° C. and 75% relative humidity.

As used herein "remains substantially constant" means that the concentration of sorbic acid preservative in an IRM-containing formulation does not decrease by more than 15% of the initial concentration (i.e., its concentration when initially formulated) when stored for at least 6 months at 40° C. and 75% relative humidity. Preferably, the concentration of the sorbic acid preservative in an IRM-containing formulation does not decrease by more than 10% of the initial concentration when stored for at least 6 months at 40° C. and 75% relative humidity. More preferably, the concentration of the sorbic acid preservative in an IRM-containing formulation does not decrease by more than 5% of the initial concentration when stored for at least 6 months at 40° C. and 75% relative humidity.

In certain embodiments, formulations described herein can be in the form of an oil-in water emulsion such as a cream or a lotion. Such an emulsion can include an oil phase that includes one or more IRM compounds, a fatty acid in an amount sufficient to solubilize the IRM compound(s), a hydrophobic, aprotic component; and an aqueous phase that includes a preservative system, and a hydrophilic viscosity enhancing agent. Such components, as well as all others of the formulations described herein, are preferably pharmaceutically acceptable.

Preservative System

In certain embodiments, formulations used in delivering 2-methyl1(2-methylpropyl)1H-imidazo[4,5-c][1,5]naphthyridin-4-amine include a preservative system. The preservative system includes one or more compounds that inhibit microbial growth (e.g., fungal and bacterial growth) within the formulation (for example, during manufacturing and use).

Typically, a preservative system includes at least one preservative compound chosen from methylparaben, ethylparaben, propylparaben, phenoxyethanol, iodopropynyl butylcarbamate, sorbic acid, a fatty acid monoester of glycerin such as glycerol monolaurate (e.g., poly(ethylene glycol)(4)monolaurate), and a fatty acid monoester of propylene glycol such as propylene glycol monocaprylate.

In certain embodiments, the preservative system can include at least one preservative compound chosen from sorbic acid, esters or salts thereof, such as, for example, isopropyl sorbate, calcium sorbate, potassium sorbate, sodium sorbate, and triethanolamine sorbate. Combinations of these may be used in formulations of the present invention. Such preservatives adversely affect the stability of the formulations as described herein.

In certain embodiments, in addition to the sorbic acid preservative, the preservative system will generally include at least one additional (i.e., secondary) preservative compound, such as, for example, methylparaben, ethylparaben, propylparaben, butylparaben, and phenoxyethanol. Various combinations of these compounds can be included in the preservative system. In some embodiments of the invention, the secondary preservative compound is methylparaben.

The preservative system may also include a preservative enhancing solubilizer which enhances the solubility of the preservative in the aqueous phase, examples of which include diethylene glycol monoethyl ether, propylene glycol, and poly(ethylene glycol)(4)monolaurate. Combinations of such enhancing solubilizers can be used in formulations of the present invention.

According to the present invention, a preservative such as a sorbic acid preservative (i.e., sorbic acid, esters or salts thereof, or combinations thereof) is preferably present in a formulation in an amount of at least 0.005% by weight, more preferably at least 0.01% by weight, even more preferably at least 0.02% by weight, even more preferably at least 0.05% by weight, and even more preferably at least 0.08% by weight, based on the total weight of the formulation. The preservative is preferably present in a formulation in an amount of no greater than 1% by weight, more preferably no greater than 0.5% by weight, even more preferably no greater than 0.2% by weight, even more preferably no greater than 0.12% by weight, and even more preferably, no greater than 0.10% by weight, based on the total weight of the formulation.

In some embodiments of the invention, the secondary preservative compound is present in an amount of at least 0.01% by weight, such as for example, at least 0.02%, at least 0.03%, at least 0.04%, and at least 0.05%, by weight based on the total weight of the formulation. In other embodiments of the invention the secondary preservative compound is present in an amount of at most 0.5%, such as for example, at most 0.4%, at most 0.3%, and at most 0.2%, by weight based on the total weight of the formulation.

In some embodiments of the present invention, propylene glycol is present in an amount of at least 1.0% by weight, such as for example, at least 2.0%, at least 3.0%, at least 4.0%, and at least 5.0%, by weight based on the total weight of the formulation. In other embodiments of the present invention, propylene glycol is present in at most 10.0% by weight, such as for example, at most 8.0%, at most 6.0%, and at most 5.0%, by weight based on the total weight of the formulation.

Antioxidants

In certain embodiments, formulations used in delivering 2-methyl1(2-methylpropyl)1H-imidazo[4,5-c][1,5]naphthyridin-4-amine include an antioxidant. In particular, the stability issue of the IRM/sorbic acid preservative combination can be addressed through the addition of one or more antioxidants. Antioxidants suitable for use herein are those that inhibit the autoxidation of the sorbic acid preservative. In particular, antioxidants having hydrogen atom donating functionality have demonstrated much greater improvement than others. Although not intending to be limiting, it is believed that antioxidants react with autoxidation intermediates (typically, radicals) of the sorbic acid preservative to form products that do not react with the IRM.

Suitable antioxidants are those that are pharmaceutically acceptable and described in the International Cosmetic Ingredient Dictionary and Handbook, Ninth Edition, Volume 4, 2002, and in the USP NF 2004: The United States Pharmacopeia, $27^{th}$ Revision and The National Formulary, $22^{nd}$ Edition.

Examples of suitable antioxidants include ascorbic acid (D and/or L enantiomers), ascorbyl palmitate (D and/or L enantiomers), butylated hydroxyanisole (BHA), butylated hydroxytoluene (BHT), cysteine (D and/or L enantiomers), propyl gallate, sodium formaldehyde sulfoxylate, sodium thiosulfate, sulfur dioxide, and tocopherol.

Preferred antioxidants are those containing hydrogen atom donating functional groups. Examples of such antioxidants include ascorbic acid, ascorbyl palmitate, BHT, BHA, cysteine, propyl gallate, sodium formaldehyde sulfoxylate, and tocopherol.

More preferred antioxidants are those containing aromatic hydroxy groups capable of hydrogen atom donation. Examples of such antioxidants include BHA, BHT, propyl gallate, and tocopherol.

Most preferred antioxidants are BHA and BHT, which can be used in combination.

According to the present invention, the antioxidant is preferably present in a formulation in an amount of at least 0.001% by weight, more preferably at least 0.005% by weight, even more preferably at least 0.008% by weight, and even more preferably at least 0.01% by weight, based on the total weight of the formulation. The antioxidant is preferably present in a formulation in an amount of no greater than 0.3% by weight, more preferably no greater than 0.2% by weight, and even more preferably no greater than 0.012% by weight, and even more preferably no greater than 0.1% by weight, based on the total weight of the formulation.

According to the present invention, the sorbic acid preservative (i.e., sorbic acid/ester/salt) to antioxidant weight ratio is preferably at least 1:20, more preferably at least 1:1, and even more preferably at least 5:1. The sorbic acid to antioxidant weight ratio is preferably no greater than 1000:1, more preferably no greater than 20:1, and even more preferably no greater than 10:1.

Chelating Agents

In certain embodiments, formulations used in delivering 2-methyl1(2-methylpropyl)1H-imidazo[4,5-c][1,5]naphthyridin-4-amine include a chelating agent. The chelating agent functions to stabilize the antioxidant(s) present in the formulation.

Chelating agents are compounds that complex with metal ions. Suitable chelating agents are those that are pharmaceutically acceptable and described in the International Cosmetic Ingredient Dictionary and Handbook, Ninth Edition, Volume 4, 2002.

Suitable chelating agents include ethylenediaminetetraacetic acid (EDTA) and citric acid, hydrates thereof, salts thereof, and hydrates of the salts thereof. Examples of such chelating agents include ethylenediaminetetraacetic acid disodium salt, ethylenediaminetetraacetic acid disodium salt dihydrate, and citric acid monohydrate. Various combinations of chelating agents can be used if desired.

According to the present invention, if included, the chelating agent is preferably present in a formulation in an amount of at least 0.001% by weight, more preferably at least 0.005% by weight, even more preferably at least 0.01% by weight, and even more preferably at least 0.05% by weight, based on the total weight of the formulation. The chelating agent is preferably present in a formulation in an amount of no greater than 0.2% by weight, and more preferably no greater than 0.1% by weight, based on the total weight of the formulation.

According to the present invention, if included, the antioxidant to chelating agent weight ratio is preferably at least 1:200, more preferably at least 1:10, and even more preferably at least 1:5. The antioxidant to chelating agent weight ratio is preferably no greater than 300:1, more preferably no greater than 10:1, and even more preferably no greater than 2:1.

Fatty Acids

In certain embodiments, formulations used in delivering 2-methyl1(2-methylpropyl)1H-imidazo[4,5-c][1,5]naphthyridin-4-amine include a fatty acid. As used herein, the term "fatty acid" means a carboxylic acid, either saturated or unsaturated having 6 to 28 carbon atoms, such as, for example, from 10 to 22 carbon atoms. Non-limiting examples of such fatty acids include isostearic acid, oleic acid, and linear- or branched-chain carboxylic acids of 6 to 18 carbon atoms.

The fatty acid may be present in the formulation in an amount sufficient to solubilize the IRM compound. In certain embodiments, the amount of the fatty acid is at least 0.05% by weight, at least 1.0% by weight, at least 3.0% by weight, at least 5.0%, at least 10%, at least 15%, or at least 25%, based on the total weight of the formulation. In certain embodiments, the amount of the fatty acid is at most 40% by weight, at most 30% by weight, at most 15% by weight, or at most 10%, based on the total weight of the formulation. The fatty acid component of the formulation can comprise one or more fatty acids.

Hydrophobic Component

In certain embodiments, formulations used in delivering 2-methyl(2-methylpropyl)1H-imidazo[4,5-c][1,5]naphthyridin-4-amine include a hydrophobic, aprotic component miscible with the fatty acid and comprising a hydrocarbyl group of 7 or more carbon atoms. By "hydrophobic" is meant that the component is essentially insoluble in water, i.e. immiscible with water and unable to form a micelle in water, and does not contain polyoxyethylene or acid salt groups. Preferably the hydrophobic, aprotic component has a hydrophilic lipophilic balance (HLB) of less than 2. The HLB of a component may be determined as described, for example, in Attwood, D., Florence, A. T. Surfactant Systems: Their Chemistry, Pharmacy, and Biology; New York: Chapman & Hall, 471-473, 1983. By "aprotic" is meant that the component cannot donate a proton to the IRM and does not contain groups such as carboxyl, hydroxy, primary and secondary amino, primary and secondary amido, or quaternary ammonium groups. Preferably this component has a pKa of at least 14.2 and does not substantially solubilize or form a complex such as an acid-base pair or complex or a hydrogen bond complex with the IRM compound. By "not substantially" is meant that the ratio of the IRM compound's solubility in the hydrophilic, aprotic component to that in isostearic acid is less than 1:40.

Formulations intended for dermal or topical use typically have amounts of an oil phase and a hydrophobic, aprotic component sufficient to provide desirable qualities such as spreadability and feel.

Examples of useful hydrophobic, aprotic components include but are not limited to fatty acid esters, for example, isopropyl mysristate, isopropyl palmitate, diisopropyl dimer dilinoleate; medium-chain (e.g., 8 to 14 carbon atoms) triglycerides, for example, caprylic/capric triglyceride; cetyl esters; hydrocarbons of 8 or more carbon atoms, for example, light mineral oil, white petrolatum; and waxes, for example, beeswax. In some embodiments, the hydrophobic, aprotic component is chosen from one or more of isopropyl mysristate, isopropyl palmitate, caprylic/capric triglyceride, and diisopropyl dimer dilinoleate. Various combinations of such hydrophobic, aprotic components can be used if desired.

In certain embodiments, the amount of the hydrophobic, aprotic component is at least 1.0% by weight, at least 3.0% by weight, at least 5.0% by weight, or at least 10% by weight, based on the total weight of the formulation. In certain embodiments, the amount of the hydrophobic, aprotic component is at most 30% by weight, at most 15% by weight, or at most 10% by weight, based on the total weight of the formulation.

The weight ratio of the hydrophobic, aprotic component to the fatty acid can be 0.025:1 to 600:1, for example, 0.5:1 to 50:1, and 2:1 to 30:1. The combined amount (weight percent of the total topical formulation weight) of the hydrophobic, aprotic component and the fatty acid can be 2% to 50% by weight, for example 2% to 30%, 5% to 30%, 5% to 20%, and 10% to 20%.

Viscosity Enhancing Agent

In certain embodiments, formulations used in delivering 2-methyl1-(2-methylpropyl)1H-imidazo[4,5-c][1,5]naphthyridin-4-amine can also include a hydrophilic viscosity enhancing agent. Examples of suitable hydrophilic viscosity enhancing agents include cellulose ethers such as hydroxypropylmethylcellulose, hydroxyethylcellulose, hydroxypropylcellulose, and carboxymethylcellulose; polysaccharide gums such as xanthan gum; and homopolymers and copolymers of acrylic acid crosslinked with allyl sucrose or allyl pentaerythriol such as those polymers designated as carbomers in the United States Pharmacopoeia. Suitable carbomers include, for example, those available as CARBOPOL 934P, CARBOPOL 971P, CARBOPOL 940, CARBOPOL 974P, CARBOPOL 980, and PEMULEN TR-1 (USP/NF Monograph; Carbomer 1342), all available from Noveon, Cleveland, Ohio. In one embodiment of the present invention, the viscosity enhancing agent is chosen from CARBOPOL 974P and 980.

In certain embodiments, the amount of the viscosity enhancing agent, when used, is at least 0.1% by weight, at least 0.2% by weight, at least 0.5% by weight, at least 0.6% by weight, at least 0.7% by weight, at least 0.9% by weight, or at least 1.0% by weight, based on the total weight of the formulation. In certain embodiments, the amount of the viscosity enhancing agent, when used, is at most 10% by weight, at most 5.0% by weight, at most 3.0% by weight, at most 2.0% by weight, or at most 1.5% by weight, based on the total weight of the formulation.

Emulsifier

In certain embodiments, formulations used in delivering 2-methyl-1-(2-methylpropyl)-1H-imidazo[4,5-c][1,5]naphthyridin-4-amine include an emulsifier. Suitable emulsifiers include non-ionic surfactants such as, for example, polysorbate 60, sorbitan monostearate, polyglyceryl-4 oleate, polyoxyethylene(4) lauryl ether, etc. In certain embodiments, the emulsifier is chosen from poloxamers (e.g., PLURONIC F68, also known as POLOXAMER 188, a poly(ethylene glycol)-block-polypropylene glycol)-block-poly(ethylene glycol), available from BASF, Ludwigshafen, Germany) and sorbitan trioleate (e.g., SPAN 85 available from Uniqema, New Castle, Del.).

If included, the emulsifier is generally present in an amount of 0.1% to 10% by weight of total formulation weight, for example, from 0.5% to 5.0% by weight, and from 0.75% to 3.5% by weight. In certain embodiments, the amount of the emulsifier, if used, is present in an amount of at least 0.1% by weight, at least 0.5% by weight, at least 0.75% by weight, at least 1.0% by weight, at least 2.5% by weight, at least 3.5% by weight, or at least 5.0% by weight, based on the total weight of the formulation. In certain embodiments, the amount of the emulsifier, if used, is present in an amount of at most 10% by weight, at least 5.0% by weight, or at most 3.5% by weight, based on the total weight of the formulation.

In certain embodiments, formulations used in delivering 2-methyl1-(2-methylpropyl)1H-imidazo[4,5-c][1,5]naphthyridin-4-amine include a pH adjuster. Suitable pH adjusters include organic bases and inorganic bases such as, for example, KOH and NaOH (e.g., aqueous formulations). The pH of the topical formulations of the present invention generally ranges from 3.5 to 7.0. In one embodiment, the pH of the topical formulations of the present invention can range from 4.0 to 6.0, preferably 5.0.

Illustrative Formulations

Formulations of the present invention are aqueous based. The water used is typically purified water. Preferred aqueous formulations of the present invention are as follows.

In one embodiment of the present invention, a pharmaceutical formulation includes: 0.3% by weight of 2-methyl-1-(2-methylpropyl)-1H-imidazo[4,5-c][1,5]naphthyridin-4-amine;
   0.02% by weight to 0.2% by weight of a sorbic acid preservative selected from the group consisting of sorbic acid, esters thereof, salts thereof, and combinations thereof;
   0 to 10.0% by weight of propylene glycol;
   0.05% by weight to 0.2% by weight of methylparaben;
   0.001% by weight to 0.2% by weight of butylated hydroxyanisole, butylated hydroxytoluene, or combinations thereof;
   0 to 0.1% by weight of ethylenediaminetetraacetic acid, a hydrate thereof, a salt thereof, a hydrate of a the salt thereof, or combinations thereof;
   1% by weight to 30% by weight of isostearic acid;
   1% by weight to 15% by weight of a medium-chain triglyceride;
   0.2% by weight to 2.0% by weight of a carbomer;
   0.1% by weight to 6.0% by weight of a poloxamer; and water;
   wherein the formulation has a pH of 4.0 to 6.0 and the weight percentages are based on the total weight of the formulation.

In one embodiment, a pharmaceutical formulation includes:
   0.3% by weight of 2-methyl-1-(2-methylpropyl)-1H-imidazo[4,5-c][1,5]naphthyridin-4-amine;
   0.15% by weight sorbic acid;
   5.0% by weight propylene glycol; 0.2% by weight methylparaben;
   0.1% by weight butylated hydroxyanisole;
   0.05% by weight ethylenediaminetetraacetic acid disodium salt dihydrate;
   7.0% by weight isostearic acid;
   4.0% by weight of caprylic/capric triglyceride;
   1.0% by weight of a carbomer;
   3.5% by weight of a poloxamer;
   0.8% by weight of an aqueous solution of 20% by weight NaOH in water; and
   77.9% by weight water;
   wherein the weight percentages are based on the total weight of the formulation.

In one embodiment, a pharmaceutical formulation includes:
   0.3% by weight of 2-methyll(2-methylpropyl)-1H-imidazo[4,5-c][1,5]naphthyridin-4-amine;
   0.1% by weight sorbic acid;
   5.0% by weight propylene glycol;
   0.2% by weight methylparaben;
   0.01% by weight butylated hydroxyanisole;
   0.05% by weight ethylenediaminetetraacetic acid disodium salt dihydrate;
   7.0% by weight isostearic acid;
   4.0% by weight of caprylic/capric triglyceride;
   1.0% by weight of a carbomer;
   3.5% by weight of a poloxamer;
   0.8% by weight of an aqueous solution of 20% by weight NaOH in water;
   and 78.0% by weight water;
   wherein the weight percentages are based on the total weight of the formulation.

EXAMPLES

The following Examples are provided to further describe various IRM formulations and methods according to the invention. The examples, however, are not intended to limit the formulations and methods within the spirit and scope of the invention.

Test Methods

IRM Compound 1 Content

A gradient reversed phase high performance liquid chromatography (HPLC) method was used to determine the amount of 2-methyl1(2-methylpropyl)1H-imidazo[4,5-c][1,5]naphthyridin-4-amine (IRM Compound 1) in cream formulations using BHA and BHT as the antioxidants.

HPLC parameters: Analytical column: ZORBAX Bonus RP, 3.5 micron particle, 150×4.6 mm (available from Agilent Technologies, Wilmington, Del., USA); Column temperature: 35° C.; Detector: UV at 240 nm; Flow Rate: 1.0 mL/min; Injection volume: 30 µL; Mobile phase A: 0.05% trifluoroacetic acid in water; Mobile Phase B: 0.05% trifluoroacetic acid in acetonitrile; Data acquisition time: 25 minutes; HPLC run time: 35 minutes. Gradient program: 0 minutes: 80% mobile phase A, 20% mobile phase B; 5 minutes: 80% mobile phase A, 20% mobile phase B; 15 minutes: 75% mobile phase A, 25% mobile phase B; 25 minutes: 35% mobile phase A, 65% mobile phase B; 28 minutes: 10% mobile phase A, 90% mobile phase B; 29 minutes: 80% mobile phase A, 20% mobile phase B; 35 minutes: 80% mobile phase A, 20% mobile phase B.

Sample solution: A portion of the cream formulation (2500 mg for creams containing 0.03% IRM; 1500 mg for creams containing 0.1% IRM; and 500 mg for creams containing 0.3% IRM) was accurately weighed into a volumetric flask (50 mL for creams containing 0.03% IRM; 100 mL for creams containing 0.1 or 0.3% IRM). Approximately 40 mL of diluent (prepared by combing 200 parts of acetonitrile, 790 parts water, and 10 parts phosphoric acid, all parts by volume) was added to the 50 mL flask or 80 mL to the 100 mL flask. The flask was shaken or vortexed to dislodge any cream from the neck of the flask and then sonicated with occasional shaking for 10 minutes or until the cream was completely dispersed. The solution was allowed to cool to ambient temperature and then diluted to volume with diluent. A portion of the solution was filtered using a syringe equipped with a 0.2 micron PTFE filter to provide the sample solution.

Sorbic Acid and BHA Content

A gradient reversed phase high performance liquid chromatography (HPLC) method was used to determine the amount of sorbic acid and BHA in cream formulations containing IRM Compound 1.

HPLC parameters: Analytical column: ZORBAX Bonus RP, 3.5 micron particle, 150×4.6 mm; Column temperature: 35° C.; Detector: UV at 285 nm; Flow Rate: 1.0 mL/min; Injection volume: 25 µL; Mobile phase A: 0.05% trifluoroacetic acid in water; Mobile Phase B: 0.05% trifluoroacetic acid in acetonitrile; Data acquisition time: 12 minutes; HPLC run time: 18 minutes.

Gradient program: 0 minutes: 60% mobile phase A, 40% mobile phase B; 10 minutes: 5% mobile phase A, 95% mobile phase B; 12 minutes: 5% mobile phase A, 95% mobile phase B; 13 minutes: 60% mobile phase A, 40% mobile phase B; 18 minutes: 60% mobile phase A, 40% mobile phase B.

Sample solution: A portion (approximately 1000 mg) of the cream formulation was accurately weighed into a 100 mL volumetric flask. Approximately 80 mL of diluent (prepared by combining 600 parts of acetonitrile, 400 parts of water, and 1 part trifluoroacetic acid, all parts by volume) was added and the flask was sonicated with occasional shaking for 10 minutes or until the cream was well dispersed. The solution was allowed to cool to ambient temperature and then diluted to volume with diluent. A portion of the solution was filtered using a syringe equipped with a 0.45 micron PTFE filter to provide the sample solution.

Preparation of Cream Formulations

The cream formulations in the Examples below were prepared using the following general method.

Oil phase preparation: The IRM compound and the BHA or BHT were dissolved in the isostearic acid and medium chain triglycerides, with heat if necessary. Generally the CARBOPOL 980 was then dispersed in the oil phase.

Water phase preparation: Edetate disodium dihydrate, methylparaben, sorbic acid, propylene glycol, and POLOXAMER 188 were added to the water and mixed until dissolved, with heat if necessary. If the CARBOPOL was not dispersed in the oil phase, it was dispersed in the water phase.

Phase combination: The oil phase was added to the water phase at ambient conditions. The emulsion was then homogenized. Sodium hydroxide was added either before or after phase combination. The cream was mixed until smooth and uniform. The pH of the cream was measured and a pH adjustment was made with additional sodium hydroxide solution, if necessary, to meet the in-process target of pH 5.

Examples 1-3

Table 1 summarizes topical formulations made in accordance with the present invention in a percentage weight-by-weight basis. The formulations were packaged in aluminum tubes with an epoxy phenolic lacquer liner.

TABLE 1

| Ingredient | Ex 1 (Comparative) | Ex 2 (Comparative) | Ex 3 |
|---|---|---|---|
| 2-methyl-1-(2-methylpropyl)-1H-imidazo[4,5-c][1,5]naphthyridin-4-amine | 0.03 | 0.10 | 0.30 |
| Isostearic acid | 5.00 | 5.00 | 7.00 |
| *Medium-chain Triglycerides | 4.00 | 4.00 | 4.00 |
| CARBOPOL 980 | 1.00 | 1.00 | 1.00 |
| POLOXAMER 188 | 3.50 | 3.50 | 3.50 |
| Propylene gylcol | 5.00 | 5.00 | 5.00 |
| Methylparaben | 0.20 | 0.20 | 0.20 |
| Sorbic acid | 0.15 | 0.15 | 0.15 |
| BHA | 0.10 | 0.10 | 0.10 |
| Edetate disodium dihydrate | 0.05 | 0.05 | 0.05 |
| Sodium hydroxide Solution 20% w/w | 0.80 | 0.80 | 0.80 |
| Purified water | 80.17 | 80.10 | 77.90 |

*Caprylic/capric triglyceride available under the trade names CRODAMOL GTCC-PN (Croda, Inc) and MIGLYOL 812N (Sasol).

Example 1

Four-Week Treatment Period

A randomized, double-blind study was performed to evaluate single and multi-weekly doses of the formulations prepared above topically applied to actinic keratosis lesions on the head.

Otherwise healthy white (n=280) and one American Indian (n=1) subjects (17% female, 83% male) ranging in ages 33 to 88 years of age (median age of 66.3), inclusive, with actinic keratosis lesions on the head were enrolled in the study. Subjects had a baseline count of four to nine (median of six) actinic keratosis lesions to qualify for enrollment into the study. The actinic keratosis lesions areas were on the scalp (26%) and face (74%).

The study included a four-week treatment period followed by an eight-week post-treatment period. Subjects were randomized into either 0.03%, 0.1%, or 0.3% 2-methyl-1-(2-methylpropyl)-1H-imidazo[4,5-c][1,5]naphthyridin-4- amine formulations as described in Table 1 in one of three treatment regimens: (1) once per week (1×/Wk), two times per week (2×/Wk), and three times per week (3×/Wk).

Subjects were instructed to apply 250 milligrams of the formulation to a 25 square centimeter area on the head containing actinic keratosis lesions just prior to sleeping hours according to the dosing regimen they were assigned. The subjects were instructed to wash the treatment area prior to applying the cream, and then rub the cream into the treatment area. The subjects were instructed to leave the formulation in place for at least eight hours without occlusion.

Subjects completed interval visits at treatment initiation, 1, 2, and 4 weeks after treatment was initiated and at four and eight-weeks after the end of treatment. Subjects were monitored for erythema and other treatment site conditions during the entire 12 weeks of the study. Erythema, as assessed by study investigators, was defined as intense, moderate, mild, or no redness of the skin at the treatment site and given an intensity score of severe, moderate, mild, or none, respectively.

Figure 2:
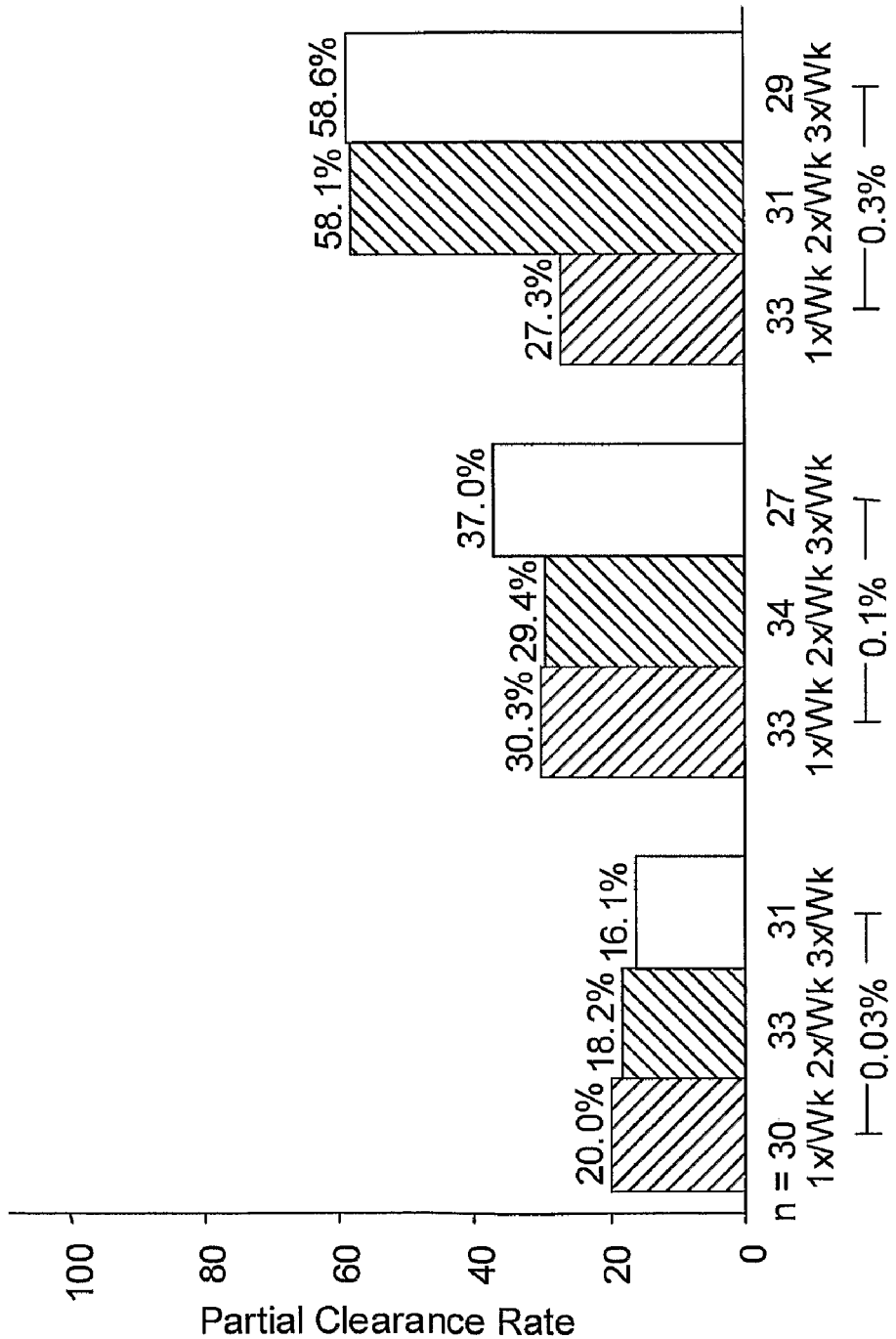
Figure 3:
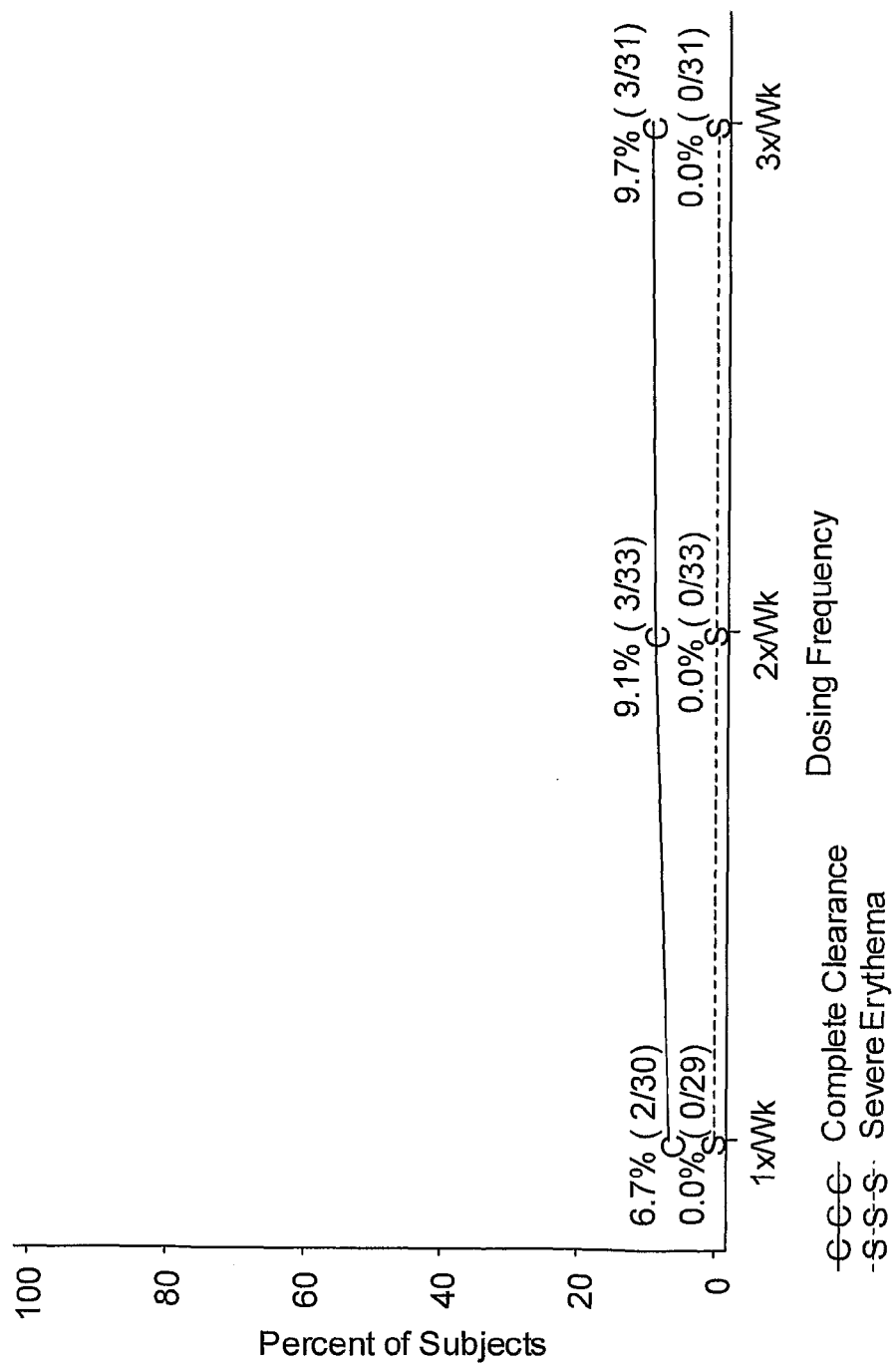
Figure 4:
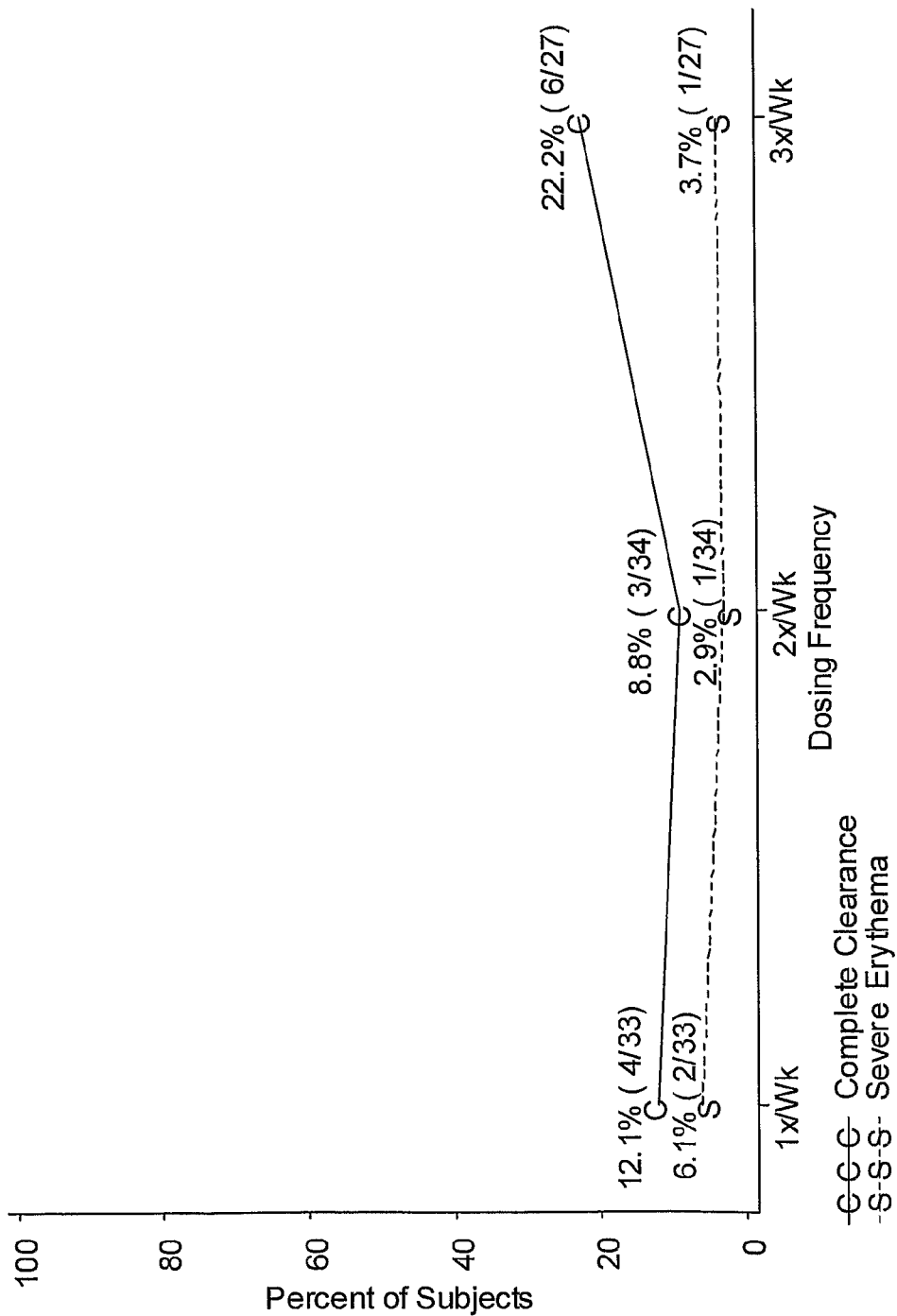
Figure 5:
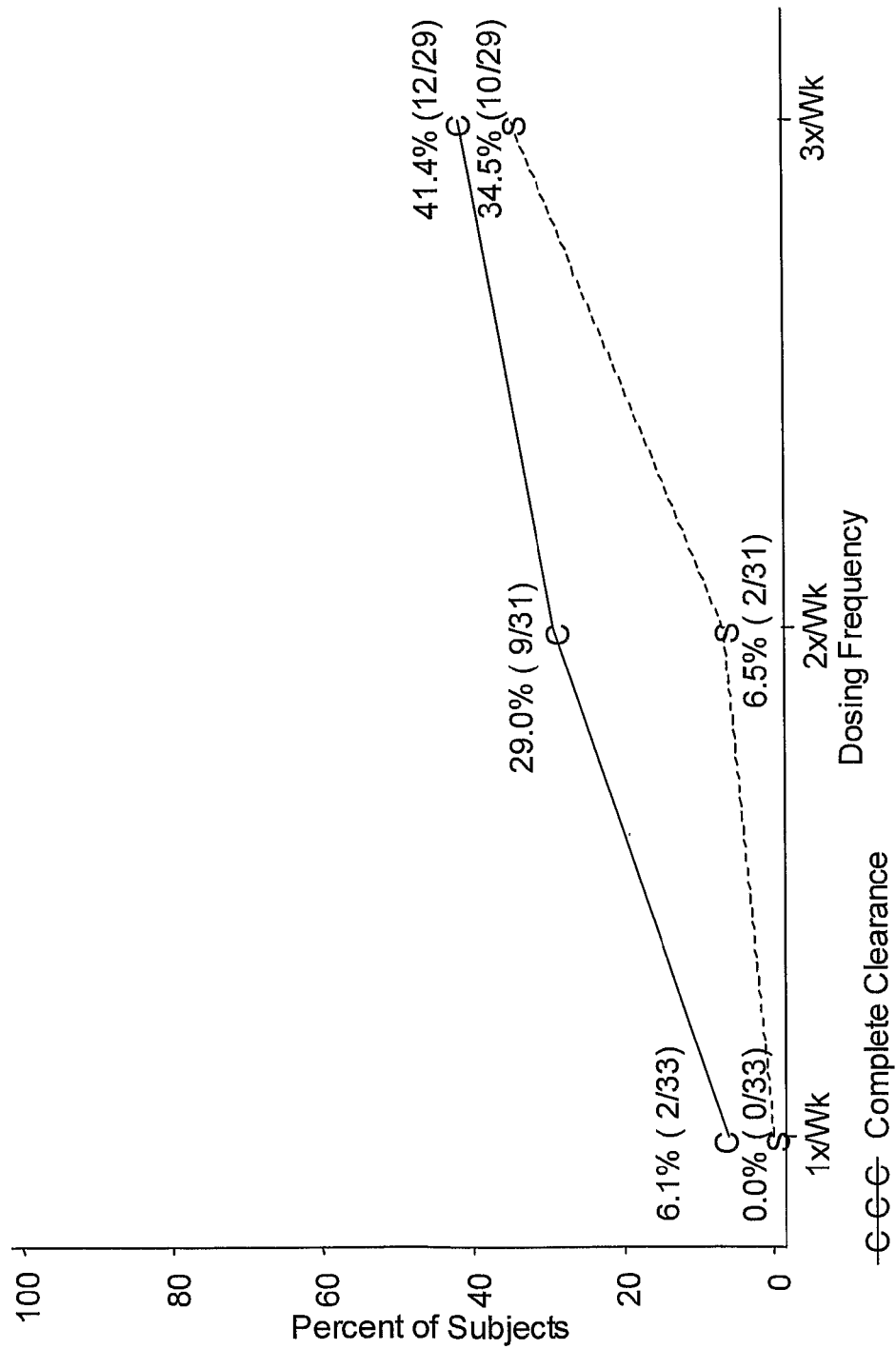

At the eight-week post-treatment visit, the treatment area was clinically evaluated for actinic keratosis lesions. Efficacy was measured as complete clearance of actinic keratosis lesions and partial clearance of actinic keratosis lesions at the eight-week post-treatment visit. The complete clearance rate is defined as the proportion of subjects at the eight-week post-treatment visit with a count of zero actinic keratosis lesions in the treatment area. The partial clearance rate is defined as the proportion of subjects at the eight-week post-treatment visit with at least 75% reduction in the number of lesions counted at baseline in the treatment area. FIGS. 1 and 2 summarize the complete clearance and partial clearance rates at the eight-week post-treatment visit, respectively. FIGS. 3, 4, and 5 summarize the therapeutic window assessment for the four-week treatment period, expressing the complete clearance and severe erythema rates for the 0.03%, 0.1%, and 0.3% compound formulations, respectively.

Example 2

Eight Week Treatment Period

A randomized, double-blind study was performed to evaluate single and multi-weekly doses of the formulations prepared above topically applied to actinic keratosis lesions on the head.

Otherwise healthy white (n=280) subjects (15% female, 85% male) ranging in ages 38 to 89 years of age (median age of 66.5), inclusive, with actinic keratosis lesions on the head were enrolled in the study. Subjects had a baseline count of four to nine (median of six) actinic keratosis lesions to qualify for enrollment into the study. The actinic keratosis lesions areas were on the scalp (36%) and face (64%).

The study included an eight-week treatment period followed by an eight-week post-treatment period. Subjects were randomized into either 0.03%, 0.1%, or 0.3% 2-methyl-1-(2-methylpropyl)-1H-imidazo[4,5-c][1,5]naphthyridin-4-amine formulations as described in Table 1 in one of three treatment regimens: (1) once per week (1×/Wk), two times per week (2×/Wk), and three times per week (3×/Wk).

Subjects were instructed to apply 250 milligrams of the formulation to a 25 square centimeter area on the head containing actinic keratosis lesions just prior to sleeping hours according to the dosing regimen they were assigned. The subjects were instructed to wash the treatment area prior to applying the cream, and then rub the cream into the treatment area. The subjects were instructed to leave the formulation in place for at least eight hours without occlusion.

Subjects completed interval visits at treatment initiation, 1, 2, 4, and 8 weeks after treatment was initiated and at four and eight-weeks after the end of treatment. Subjects were monitored for erythema and other treatment site conditions during the entire 16 weeks of the study. Erythema, as assessed by study investigators, was defined as intense, moderate, mild, or no redness of the skin at the treatment site and given an intensity score of severe, moderate, mild, or none, respectively.

Figure 6:
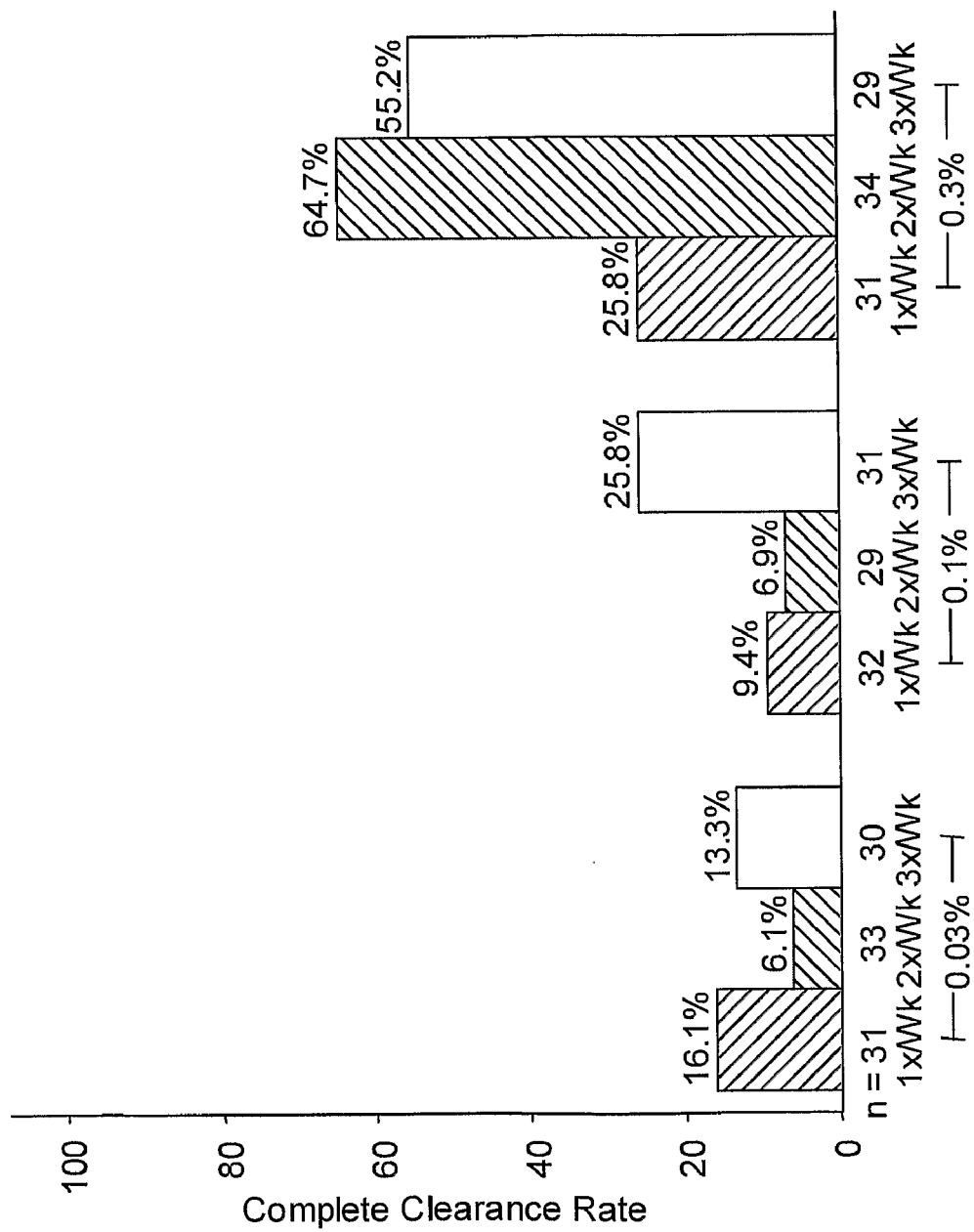
Figure 7:
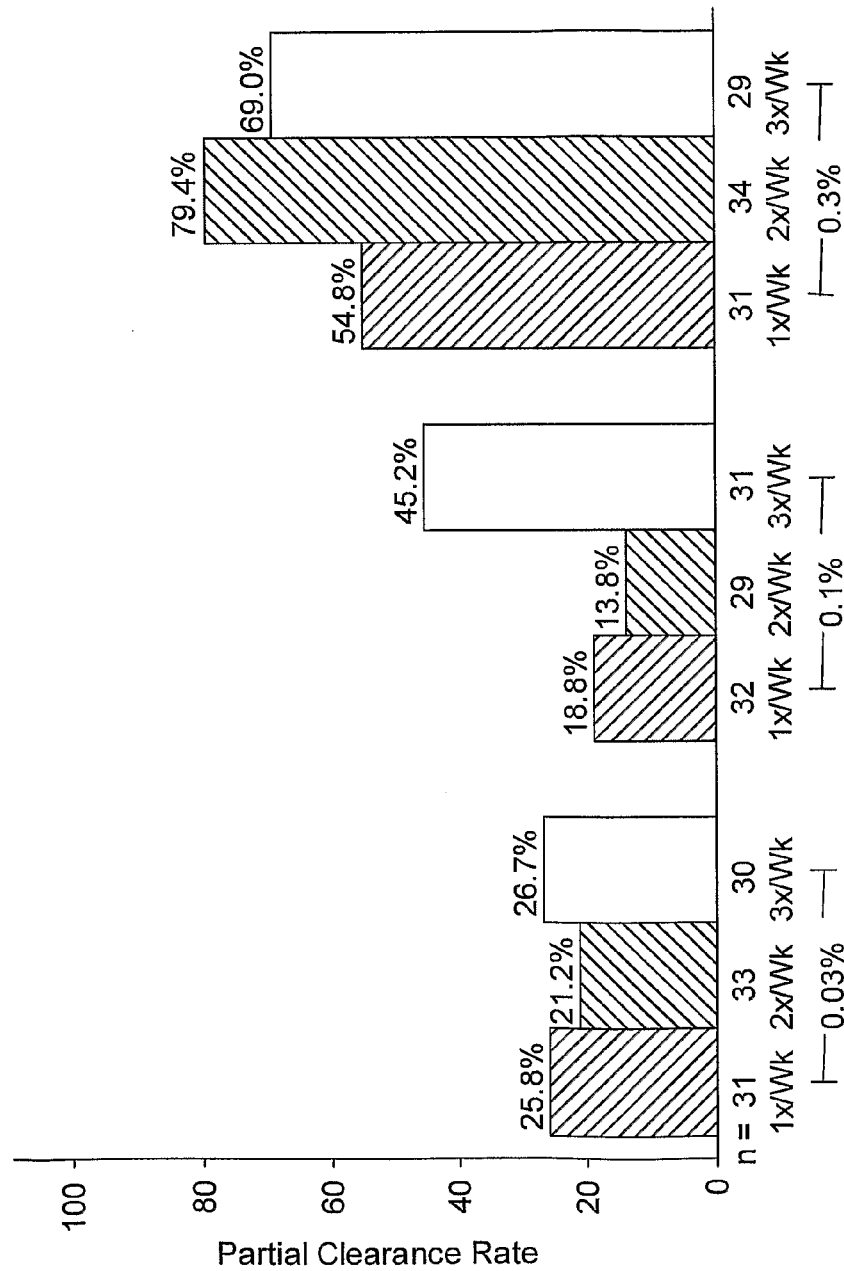
Figure 8:
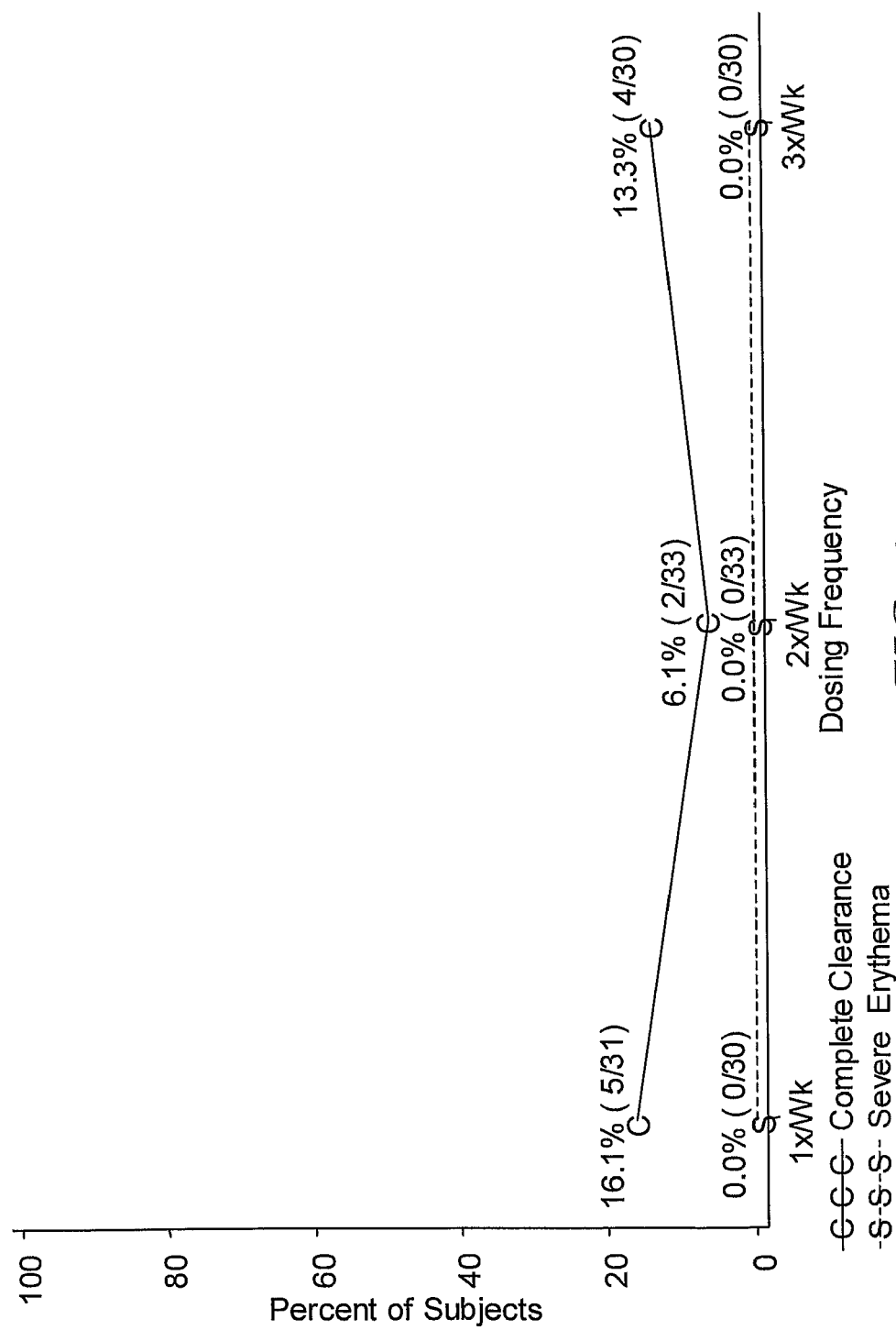
Figure 9:
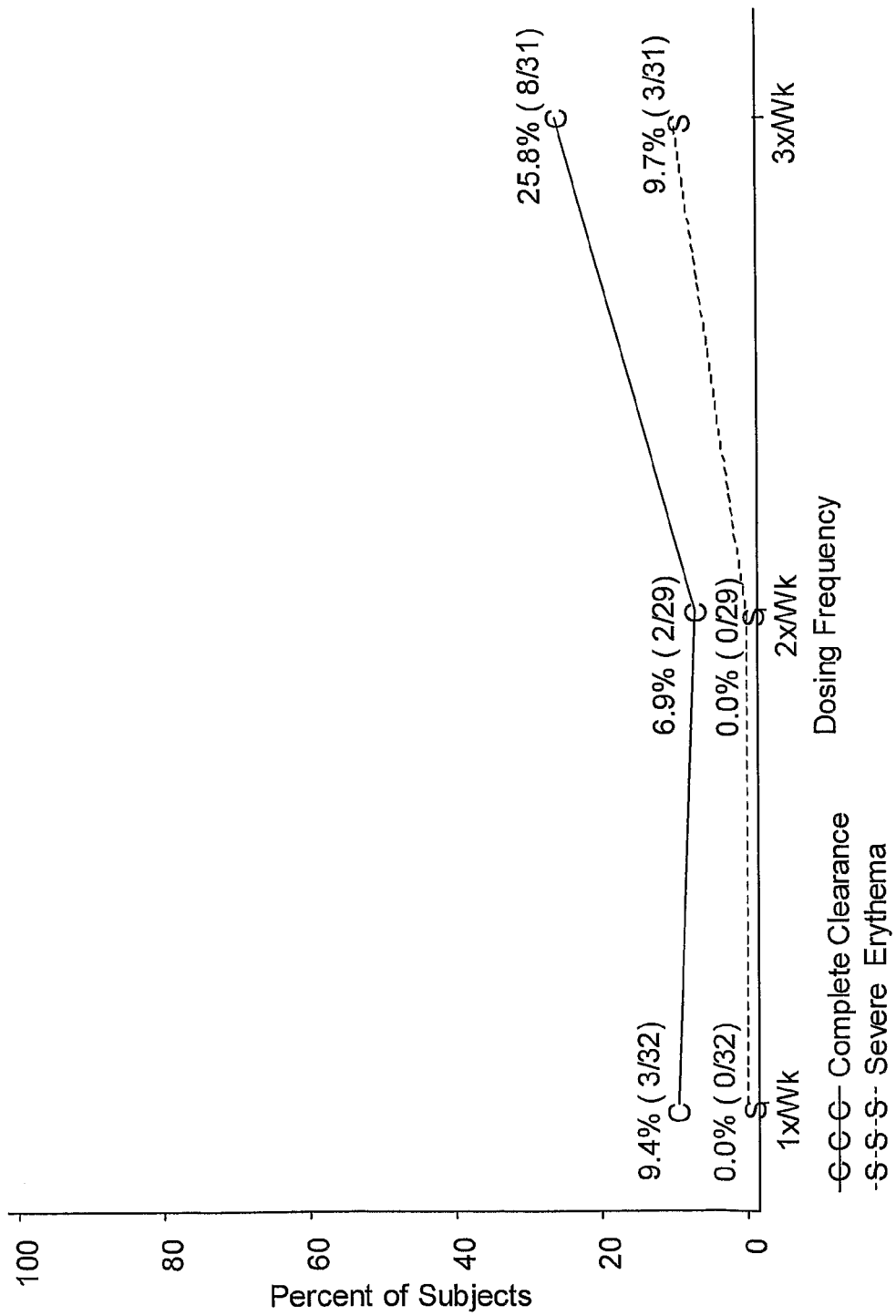
Figure 10:
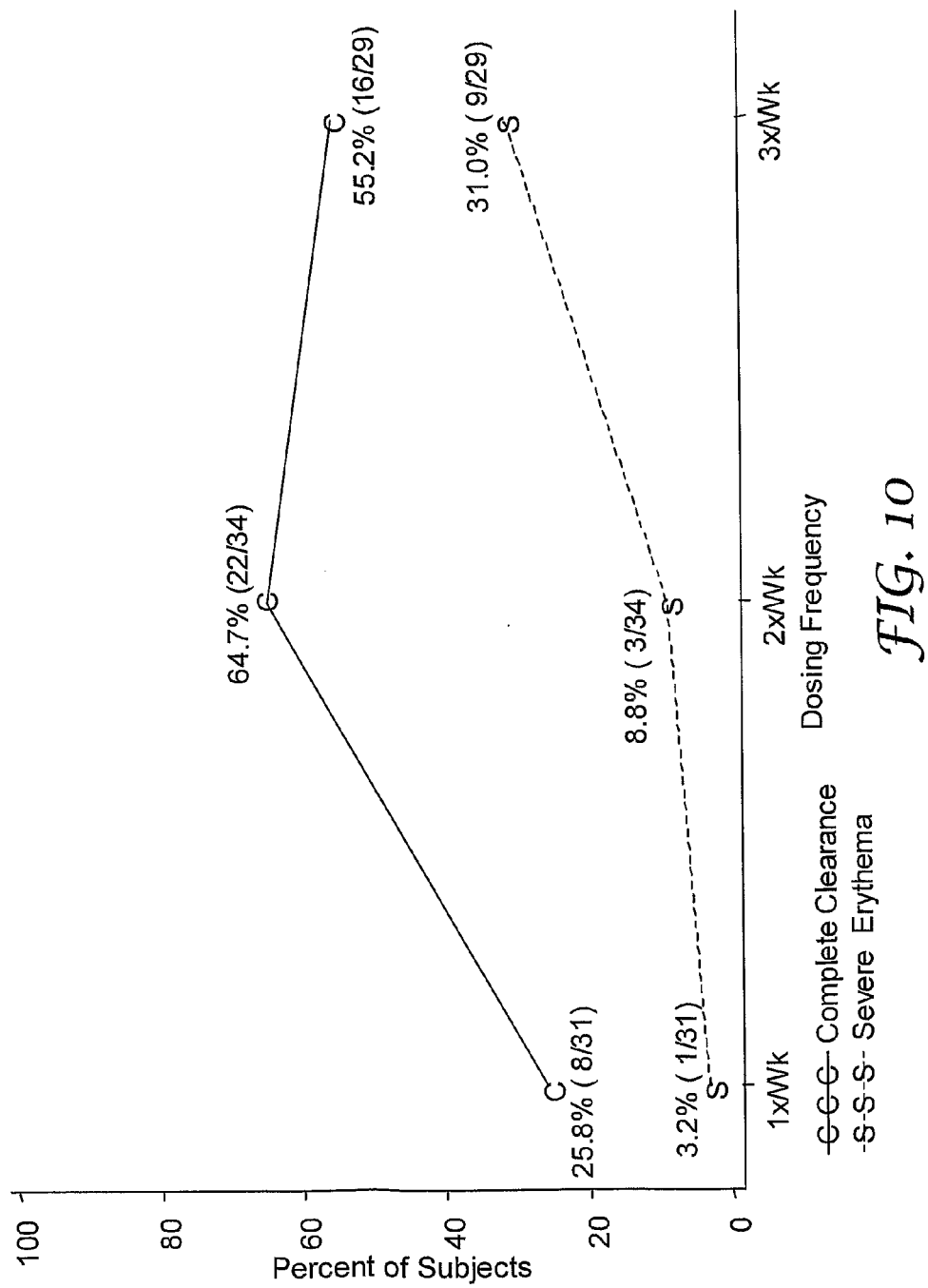

At the eight-week post-treatment visit, the treatment area was clinically evaluated for actinic keratosis lesions. Efficacy was measured as complete clearance of actinic keratosis lesions and partial clearance of actinic keratosis lesions at the eight-week post-treatment visit. The complete clearance rate is defined as the proportion of subjects at the eight-week posttreatment visit with a count of zero actinic keratosis lesions in the treatment area. The partial clearance rate is defined as the proportion of subjects at the eight-week post-treatment visit with at least 75% reduction in the number of lesions counted at baseline in the treatment area. FIGS. 6 and 7 summarize the complete clearance and partial clearance rates at the eight-week post-treatment visit, respectively. FIGS. 8, 9, and 10 summarize the therapeutic window assessment for the eight-week treatment period, expressing the complete clearance and severe erythema rates for the 0.03%, 0.1%, and 0.3% compound formulations, respectively.

Figure 11:
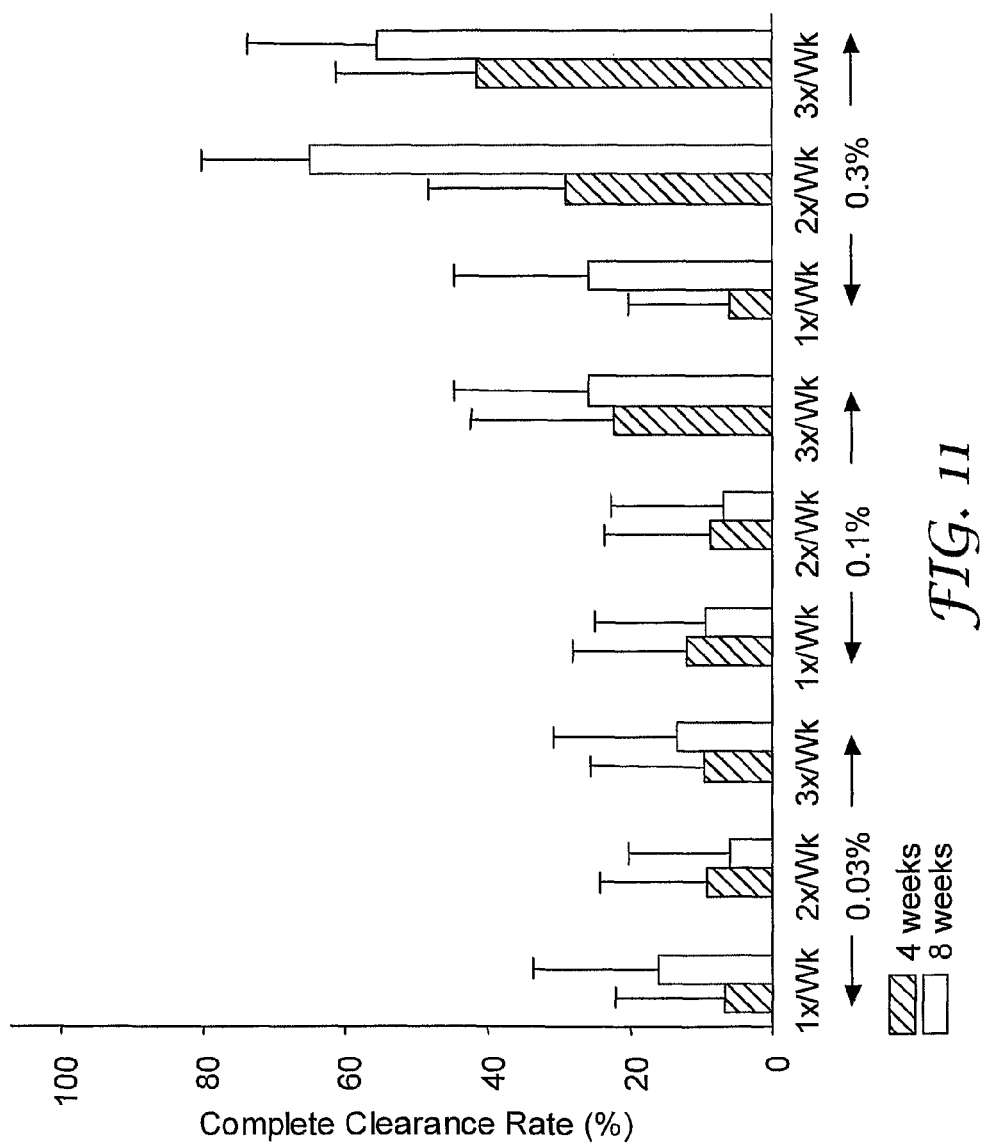

FIG. 11 summarizes the complete clearance rates of actinic keratosis lesions of the four and eight-week treatment periods.

The complete disclosures of the patents, patent documents, and publications cited herein are incorporated by reference in their entirety as if each were individually incorporated, except that if there is any apparent conflict or inconsistency the present disclosure is controlling. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

The invention claimed is:

1. A method of treating actinic keratosis, the method comprising applying topically to an actinic keratosis lesion twice per week for a duration of 8 weeks a formulation comprising:
  0.3% by weight of 2-methyl-1-(2-methylpropyl)-1H-imidazo[4,5-c][1,5]naphthyridin-4-amine;
  0.15% by weight sorbic acid;
  5.0% by weight propylene glycol;
  0.2% by weight methylparaben;
  0.1% by weight butylated hydroxyanisole;
  0.05% by weight ethylenediaminetetraacetic acid disodium salt dihydrate;
  7.0% by weight isostearic acid;
  4.0% by weight of caprylic/capric triglyceride;
  1.0% by weight of a carbomer;
  3.5% by weight of a poloxamer;
  0.8% by weight of an aqueous solution of 20% by weight NaOH in water; and
  77.9% by weight water;
  wherein the weight percentages are based on the total weight of the formulation.

2. A method of treating actinic keratosis, the method comprising applying topically to an actinic keratosis lesion twice per week for a duration of 8 weeks a formulation comprising:
- 0.3% by weight of 2-methyl-1-(2-methylpropyl)-1H-imidazo[4,5-c][1,5]naphthyridin-4-amine;
- 0.1% by weight sorbic acid;
- 5.0% by weight propylene glycol;
- 0.2% by weight methylparaben;
- 0.01% by weight butylated hydroxyanisole;
- 0.05% by weight ethylenediaminetetraacetic acid disodium salt dihydrate;
- 7.0% by weight isostearic acid;
- 4.0% by weight of caprylic/capric triglyceride;
- 1.0% by weight of a carbomer;
- 3.5% by weight of a poloxamer;
- 0.8% by weight of an aqueous solution of 20% by weight NaOH in water; and
- 78.0% by weight water;

wherein the weight percentages are based on the total weight of the formulation.

3. A method of treating a patient diagnosed with actinic keratosis, the method comprising applying topically to a treatment area comprising at least one actinic keratosis lesion or pre-actinic keratosis lesion for a treatment cycle of at least twice per week for a duration of at least 4 weeks an effective amount of a formulation comprising:
- 0.3% by weight of 2-methyl-1-(2-methylpropyl)-1H-imidazo[4,5-c][1,5]naphthyridin-4-amine (sotirimod);
- 0.15% by weight sorbic acid;
- 5.0% by weight propylene glycol;
- 0.2% by weight methylparaben;
- 0.1% by weight butylated hydroxyanisole;
- 0.05% by weight ethylenediaminetetraacetic acid disodium salt dihydrate;
- 7.0% by weight isostearic acid;
- 4.0% by weight of caprylic/capric triglyceride;
- 1.0% by weight of a carbomer;
- 3.5% by weight of a poloxamer;
- 0.8% by weight of an aqueous solution of 20% by weight NaOH in water; and
- 77.9% by weight water;

wherein the weight percentages are based on the total weight of the formulation.

4. The method of claim 3 further comprising applying the formulation at least twice per week for eight weeks.

5. The method of claim 3 further comprising applying the formulation at least three times per week for four weeks.

6. The method of claim 3 further comprising applying the formulation at least three times per week for eight weeks.

7. The method of claim 3, wherein the method comprises applying the formulation to the treatment area prior to sleeping hours.

8. The method of claim 3, wherein the formulation, once applied to the lesion, is left on the treatment area for about 8 hours.

9. The method of claim 3, wherein the formulation, once applied to the lesion, is left on the treatment area without occlusion.

10. The method of claim 3, wherein the formulation is applied to the treatment area with rubbing.

11. The method of claim 3, wherein prior to application, the treatment area is washed.

12. The method of claim 3, wherein at least a portion of the treatment area is located on the patient's head.

13. The method of claim 12, wherein at least a portion of the treatment area is located on the patient's face.

14. The method of claim 12, wherein at least a portion of the treatment area is located on the patient's scalp.

15. The method of claim 3, wherein the effective amount of the formulation comprises about 10 mg of the formulation applied to each square centimeter of the treatment area.

16. The method of claim 3, wherein the effective amount of the formulation comprises about 250 mg of the formulation applied to 25 cm$^2$ of the treatment area.

17. The method of claim 3, wherein the effective amount of the formulation comprises about 250 mg of the formulation.

18. The method of claim 3, wherein the treatment area comprises about 25 cm$^2$.

19. The method of claim 3, wherein the method further comprises the step of:
Conducting a first follow-up visit at approximately 8 weeks post-treatment to assess the treatment site for clinical clearance.

20. The method of claim 19, wherein clinical clearance comprises at least 75% reduction in actinic keratosis lesions or pre-actinic keratosis lesions.

21. The method of claim 19, wherein the first follow-up visit further comprises assessment of the treatment site for erythema.

22. The method of claim 19, wherein the clinical clearance comprises a response rate of at least about 58.1% for at least 75% reduction in actinic keratosis lesions or pre-actinic keratosis lesions at about 12 weeks after the four-week treatment cycle or a response rate of at least about 29.0% for 100% reduction in actinic keratosis lesions or pre-actinic keratosis lesions at about 8 weeks after the four-week treatment cycle.

23. The method of claim 19, wherein the clinical clearance comprises a response rate of about 58.6% for at least 75% reduction in actinic keratosis lesions or pre-actinic keratosis lesions at about 12 weeks after the four-week treatment cycle or a response rate of about 41.4% for 100% reduction in actinic keratosis lesions or pre-actinic keratosis lesions at about 8 weeks after the four-week treatment cycle.

24. The method of claim 19, wherein the treatment cycle comprises applying the formulation at least twice per week for eight weeks; and
wherein the clinical clearance comprises a response rate of at least about 69.0% for at least 75% reduction in actinic keratosis lesions or pre-actinic keratosis lesions at about 12 weeks after the eight-week treatment cycle or a response rate of at least about 55.2% for 100% reduction in actinic keratosis lesions or pre-actinic keratosis lesions at about 8 weeks after the eight-week treatment cycle.

25. The method of claim 19, wherein the treatment cycle comprises applying the formulation at least twice per week for eight weeks; and
wherein the clinical clearance comprises a response rate of about 79.4% for at least 75% reduction in actinic keratosis lesions or pre-actinic keratosis lesions at about 12 weeks after the four-week treatment cycle or a response rate of about 64.7% for 100% reduction in actinic keratosis lesions or pre-actinic keratosis lesions at about 8 weeks after the four-week treatment cycle.

26. The method of claim 19, wherein the first follow-up visit further comprises assessment of the treatment site for incidence of erythema.

27. The method of claim 25, wherein the incidence of erythema is about 34.5% or less.

28. The method of claim 27, wherein the incidence of erythema is about 6.5%.

29. The method of claim 25, wherein the treatment cycle comprises applying the formulation at least twice per week for eight weeks; and wherein the incidence of erythema is about 31.0% or less.

30. The method of claim 29, wherein the incidence of erythema is about 8.8%.

31. The method of claim 3, wherein the concentration of the sorbic acid in the formulation does not decrease by more than 15% of the initial concentration after the formulation is stored for at least 6 months at 40° C. and 75% relative humidity.

* * * * *